US005320640A

United States Patent [19]

Riddle et al.

[11] Patent Number: 5,320,640

[45] Date of Patent: Jun. 14, 1994

[54] CONTINUOUS PASSIVE MOTION CERVICAL SPINE THERAPY DEVICE

[75] Inventors: George E. Riddle, Clinton; Ronnie J. Withrow, Athens; George M. Cox, LaFollette; James L. Aslinger, Oliver Springs, all of Tenn.

[73] Assignee: United Apothecary, Inc., Oak Ridge, Tenn.

[21] Appl. No.: 843,805

[22] Filed: Feb. 28, 1992

Related U.S. Application Data

[63] Continuation-in-part of Ser. No. 640,945, Jan. 14, 1991, Pat. No. 5,123,916.

[51] Int. Cl.[5] .......... A61F 5/00

[52] U.S. Cl. .......... 606/242; 606/243; 5/617

[58] Field of Search .......... 606/241-245; 128/25 R; 5/613, 617, 636

[56] References Cited

U.S. PATENT DOCUMENTS

| | | | |
|---|---|---|---|
| 1,190,195 | 7/1916 | Schmidt . | |
| 1,830,071 | 11/1931 | Patton . | |
| 2,002,349 | 5/1935 | Lundeen . | |
| 2,104,745 | 1/1938 | Howell et al. . | |
| 2,152,431 | 3/1939 | Jensen . | |
| 2,179,595 | 11/1939 | McManis . | |
| 2,598,204 | 5/1952 | Allen . | |
| 2,865,367 | 12/1958 | Sorenson . | |
| 2,931,354 | 4/1960 | Sellner . | |
| 3,241,828 | 3/1966 | Adolphson et al. . | |
| 3,315,666 | 4/1967 | Sellner . | |
| 3,450,132 | 6/1969 | Ragon et al. . | |
| 3,623,480 | 11/1971 | Chisolm . | |
| 3,674,017 | 7/1972 | Stefani, Jr. . | |
| 4,144,880 | 3/1979 | Daniels . | |
| 4,404,966 | 9/1983 | Hartman | 606/242 |
| 4,445,504 | 5/1984 | Barge . | |
| 4,531,730 | 7/1985 | Chenera . | |
| 4,649,905 | 3/1987 | Barnes . | |
| 4,655,200 | 4/1987 | Knight . | |
| 4,660,549 | 4/1987 | Kowalski et al. | 606/242 |
| 4,724,828 | 2/1988 | Barnes et al. . | |
| 4,827,913 | 5/1989 | Parker . | |
| 4,834,072 | 5/1989 | Goodman . | |
| 4,960,111 | 10/1990 | Steffensmeier . | |

*Primary Examiner*—Richard J. Apley
*Assistant Examiner*—Linda C. M. Dvorak
*Attorney, Agent, or Firm*—Pitts & Brittian

[57] ABSTRACT

A continuous passive motion cervical spine therapy device (10) for passively exercising the muscles surrounding the spine for postoperative and other rehabilitative therapy. The continuous passive motion cervical spine therapy device (10) includes a frame (12) for engaging a support surface (32). A body support (14) is provided for supporting the body a patient and includes at least a first stationary support (64) for supporting at least a portion of the back of a patient and a pivoting support (78) for supporting the head of a patient. A headrest (198) is carried by the pivoting support (78). A motor (92) is provided for driving a pivoting support oscillator (18), the oscillator (18) being provided to displace the pivoting support (78) a selected angle with respect to the horizontal. A displacement adjuster (20) is connected to each oscillator (18) for altering the amplitude of displacement. A control box (22) is provided for carrying the motor controls, including at least a patient control button (24) and an emergency stop button (26). Casters (170) with locking Wheels (172) are provided to aid in easily transporting the device (10).

11 Claims, 5 Drawing Sheets

CONTINUOUS PASSIVE MOTION CERVICAL SPINE THERAPY DEVICE

This application is a continuation-in-part of my earlier filed application, Ser. No. 07/640,945 filed on Jan. 14, 1991, now U.S. Pat. No. 5,123,916.

TECHNICAL FIELD

This invention relates to the field of postoperative spinal therapy. Specifically, this invention relates to an apparatus used in the postoperative rehabilitation of the cervical spine to regain strength and function.

BACKGROUND ART

In the field of postoperative spinal therapy, it is well known that serious loss of motion, painful contractures and stiffness may occur. It is also well known that rehabilitation is difficult in that the normal collagen formation cannot occur and disorganized scar results which further impedes the healing process and recovery.

Other devices have been produced to exercise the human body for rehabilitative or other purposes. Typical of the art are those devices disclosed in U.S. Pat. No. 2,152,431 issued to S. H. Jensen on Mar. 28, 1939; U.S. Pat. No. 2,598,204 issued to R. E. Allen on May 27, 1952; and U.S. Pat. No. 3,315,666 issued to J. W. Sellnor on Apr. 25, 1967; U.S. Pat. No. 3,450,132 issued to C. A. Ragon, et al. on Jun. 17, 1969; U.S. Pat. No. 3,623,480 issued to R. F. Chisholm on Nov. 30, 1971; U.S. Pat. No. 3,674,017 issued to H. Stefani, Jr. on Jul. 4, 1972; U.S. Pat. No. 4,531,730 issued to R. Chenera on Jul. 30, 1985; U.S. Pat. No. 4,827,913 issued to A. E. Parker on May 9, 1989; and U.S. Pat. No. 4,834,072 issued to L. M. Goodman on May 30, 1989. Each of these devices is designed to exercise the human body in some fashion for strengthening, stretching, relaxing, reducing weight, or some other related function. None of these, however, is designed specifically for exercising a patient's cervical spine as a rehabilitation technique following surgery, or for patients suffering from chronic deconditioned spines. For example, the U.S. Pat. Nos. 3,623,480 ('480), 3,674,017 ('017), and 4,827,913 ('913) patents are most useful in exercising the abdomen region. However, these designs employ a single pivoting support surface, the surface being pivoted in a range from substantially the horizontal plane upward to substantially the vertical plane. The U.S. Pat. No. 4,834,072 ('072) patent discloses an invention which is specifically designed to exercise the legs in like manner by elevating the legs simultaneously or individually above or below the horizontal plane, with no other body parts being exercised. The U.S. Pat. No. 3,450,132 ('132) patent is designed to exercise the feet, legs, hips, back, arms, shoulders and neck of a patient suffering from polio or other form of paralysis or muscular disorder.

The desired exercise for postoperative cervical spinal therapy begins with the patient lying in a substantially horizontal plane, the head then being lowered to an angle below the horizontal, the buttocks, legs, and shoulders remaining stationary throughout. The head is then raised an angle above the horizontal and then lowered back to the starting position and the process repeated a desired number of times or for a desired duration. The angle to which the head is raised above the horizontal plane may be greater than, less than, or equal to the angle the head is lowered below the horizontal. The U.S. Pat. Nos. 2,152,431 ('431), 2,598,204 ('204), 3,315,666 ('666), and 4,531,730 ('730) patents disclose devices which ma be used to acquire this type of motion. However, they are not designed specifically for postoperative treatment or spinal patients and offer a much wider range of motion than is desired, along with other features unnecessary or inappropriate for such treatment. For example, the '666 patent is designed to massage a user's back or other body part, depending on how the device is employed, and requires the motion of the user to manipulate the device as opposed to an external power source. This, of course, is undesirable due to the weakened condition of the spinal patient. The '666 patent does not provide for a stationary buttocks support, thereby preventing the isolation of the desired muscles for rehabilitation. Likewise, the '730 patent is ineffective because it is designed specifically for stretching the legs of a user in order to improve leg flexibility. The '730 patent is also manually operated with no means for limiting the range of motion of each repetition.

It may be desirable for the exclusive exercise of the patient's cervical spine when operative or other therapeutic techniques are performed on this portion of the spine. Exercise of the lumbar spine may be unnecessary in these instances. Several patents are known to describe devices for the manipulation of the head in chiropractic procedures. Typical are those described in U.S. Pat. No. 4,445,504 issued to F. H. Barge on May 1, 1984; U.S. Pat. No. 4,649,905 issued to J. E. Barnes on Mar. 17, 1987; U.S. Pat. No. 4,724,828 issued to J. E. Barnes, et al., on Feb. 16, 1988; and U.S. Pat. No. 4,960,111 issued to L. A. Steffensmeier on Oct. 2, 1990. However, these devices are for the application of force to the body of a patient during chiropractic procedures such as "snapping" a patient's spine or a massage. These devices do not provide for continuous passive motion as a means for cervical spine therapy.

Therefore, it is an object of this invention to provide a means for passively exercising the muscle groups especially surrounding the cervical spine for postoperative and other rehabilitative therapy.

Another object of this invention is to provide a means whereby the normal collagen formation may occur, thus minimizing scarring and allowing a faster return to normal function and development of strength in both the muscles of function as well as the secondary support system.

Another object of this invention is to provide a means whereby the range of motion is selectable.

Another object of the present invention is to provide a means whereby the upper body may be exercised exclusively, while the lower body remains in a resting position.

Yet another object of this invention is to provide a means whereby the patient may control the operation of the device.

DISCLOSURE OF THE INVENTION

Other objects and advantages will be accomplished by the present invention which serves to passively exercise the muscle groups especially surrounding the cervical spine for postoperative and other rehabilitative therapy. The continuous passive motion cervical spine therapy device includes a frame means for engaging a support surface. The frame means is fabricated from a lightweight, rigid material such as tubular steel or the like. In the preferred embodiment, the frame means has a substantially box-shaped configuration with a length and width to support a selected size body support means. The height of the frame means is dimensioned such that a patient may easily position his/her body on the body support means, or in the case of an inambulant patient, medical attendants may easily move the patient from a typical bed to the device.

The body support means is provided for supporting the body of a patient. The body support means includes at least one stationary support means and a pivoting support means. A first stationary support means is provided to support at least a portion of the back of the patient. The first stationary support means is connected to the frame means proximate the middle portion such that the first stationary support means is elevated above the frame means. The first stationary support means of the preferred embodiment has a substantially rectangular configuration and is dimensioned to comfortably seat a patient of a selected size. In the preferred embodiment, the stationary support includes a planar member with a cushion attached to the top side for the comfort of the patient, especially when extended use is required. A second stationary support means may be provided for supporting at least the buttocks and a portion of the legs of a patient. The second stationary support means of this embodiment is substantially the same height as the first stationary support means and is further constructed similarly to the first stationary support means.

A pivoting support means is provided for supporting the head of a patient. The pivoting support means includes a member configured to restrain a patient's head, the restraining member being slidably connected to an arm pivotally connected to the frame means. The pivoting support means of the preferred embodiment is fabricated from a rigid material such as wood or sheet metal. A cushion may be provided to cover the pivoting supports for the comfort of the patient.

A drive means is provided for selectively oscillating the pivoting support means. The drive means is powered by a selected motor commonly used in the art, the speed of the motor being variably controlled. A transmission is connected between the motor and a drive shaft for controlling the rotational velocity of the drive shaft in relation to the rotational velocity of the motor. The drive shaft is connected to a pivoting support displacement means. The drive means of the preferred embodiment is connected to at least one lateral support member of the frame means.

A pivoting support displacement means is provided for oscillating the pivoting support means. The drive shaft extends from the transmission and engages a cam, a push rod being connected eccentrically to the cam. The push rod is also connected to the pivoting support means such that as the cam is rotated, the bottom end of the push rod is moved in a circular direction, causing the top end of the push rod to move in a substantially vertical direction, thus displacing the pivoting support means.

A displacement adjustment means is connected to the pivoting support displacement means for selectively altering the amplitude of displacement. In the preferred embodiment, a plurality of openings is defined by the cam, the openings being spaced apart radially away from the axle. The openings are configured to receive the selected bolt used to attach the push rod. The opening farthest from the axle has the greatest eccentricity and therefore will yield the greatest displacement of the pivoting support. Likewise, the opening closest the axle is the least eccentric and will therefore yield the least displacement.

A control box is provided for the location of the motor controls. The control box includes at least an on/off switch for the selective operation of the motor and a speed regulator for adjusting the speed of the motor. A patient control means is provided such that a patient may remotely control the speed of the drive means while using the device. The patient control means of the preferred embodiment is configured to be easily held by the user such that the desired exercise may be performed without requiring the patient to alter his position during exercise. The control button is designed to function at least as a remote on/off switch and conceivably as a speed control or other desired function. In the preferred embodiment, the patient control means is connected proximate the control box with a plug-in type jack or other conventional method. An emergency stopping means is provided to interrupt operation of the device when required. In the preferred embodiment, the emergency stopping means includes an on/off switch designed to override all other controls in order to arrest the movement of the pivoting supports.

A mobilization means is provided such that the device may be easily transported. In the preferred embodiment, the mobilization means includes a plurality of casters provided with wheel locks which are commonly known in the art. Casters are attached to the frame means at least proximate each corner of the bottom of the frame means.

BRIEF DESCRIPTION OF THE DRAWINGS

The above-mentioned features of the invention will become more clearly understood from the following detailed description of the invention read together with the drawings in which.

BEST MODE FOR CARRYING OUT THE INVENTION

Figure 1:
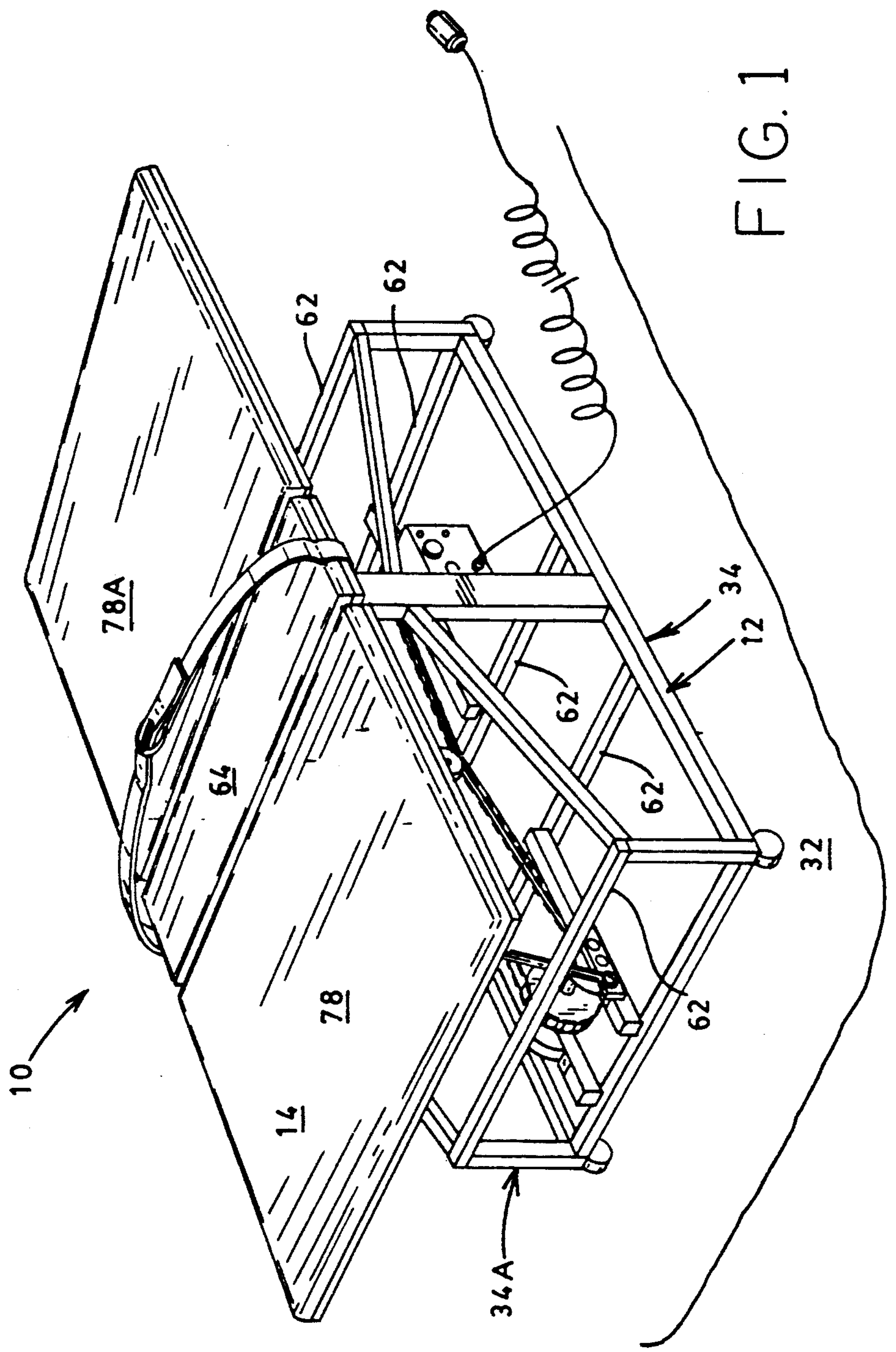
FIG. 1 is a perspective view of the spine therapy device constructed in accordance with several features of the present invention.
Figure 2:
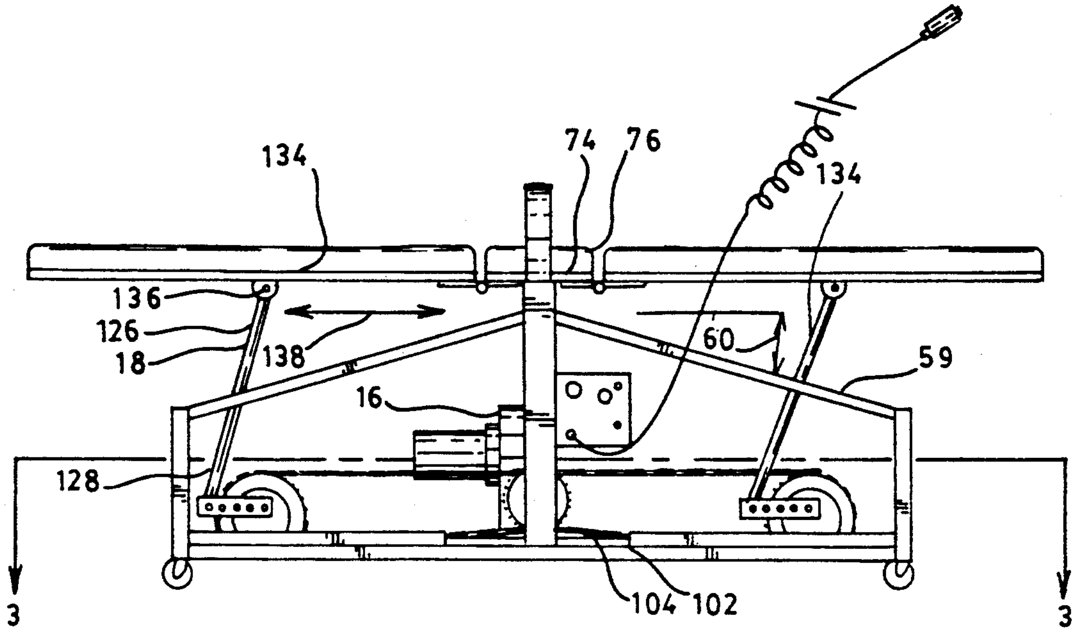
FIG. 2 illustrates a front elevation view of the spine therapy device shown in FIG. 1.
Figure 3:
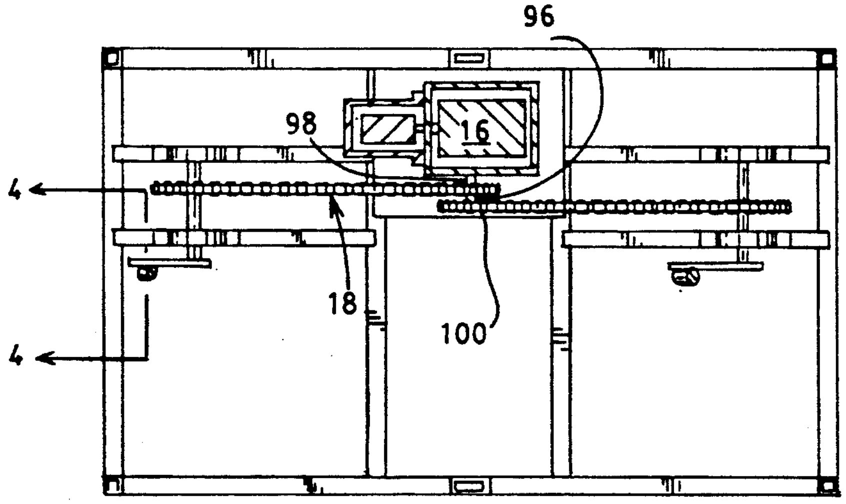
FIG. 3 is a top elevation view, in section, of the spine therapy device taken at 3—3 of FIG. 2.
Figure 4:
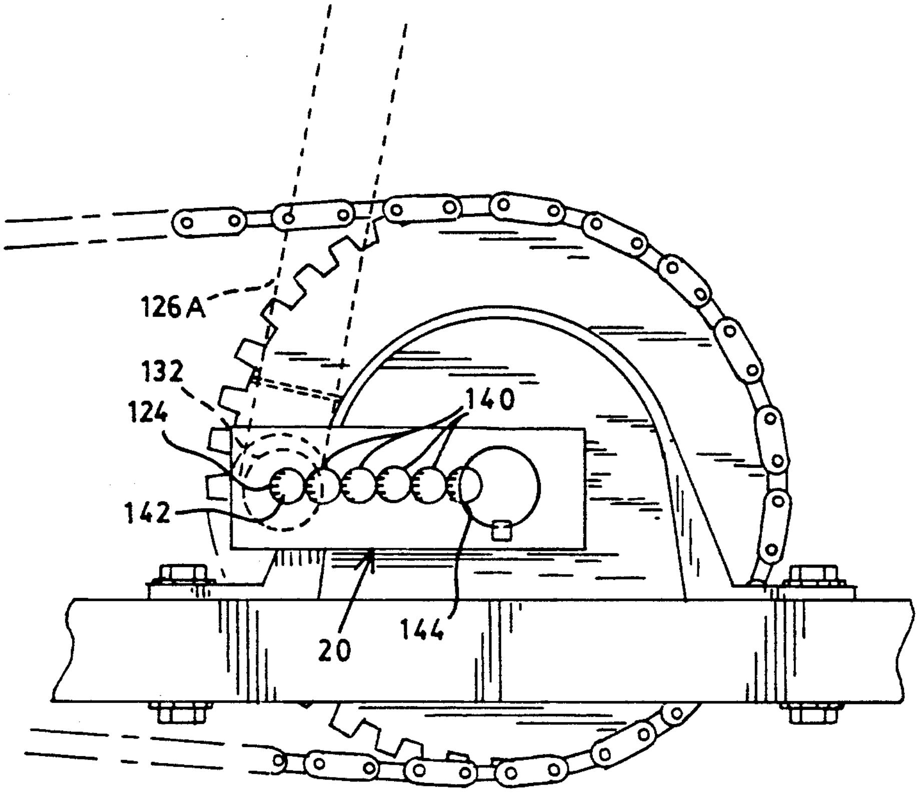
FIG. 4 illustrates a partial front elevation view of the spine therapy device showing the amplitude adjustment means, the push rod of the pivoting support displacement means being shown in phantom.

A continuous passive motion cervical spine therapy device incorporating various features of the present invention is illustrated generally at 10 in the figures. The continuous passive motion cervical spine therapy device 10 is designed for passively exercising the muscle groups especially surrounding the cervical spine for postoperative and other rehabilitative therapy such as to allow normal collagen formation to occur, thus minimizing scarring and allowing a faster return to normal function and development of strength in both the muscles of function as well as the secondary support system.

The continuous passive motion cervical spine therapy device 10 includes a frame means 12 for engaging a support surface 32. The frame means 12 is fabricated from a lightweight, rigid material such as tubular steel or the like. In the preferred embodiment, the frame means 12 has a substantially box-shaped configuration with a length and width to support a selected size body support means 14. The height of the frame means 12 is dimensioned such that a patient may easily position his/her body on the body support means 14, or in the case of an inambulant patient, medical attendants may easily move the patient from a typical bed to the continuous passive motion cervical spine therapy device 10. The frame means 12 of the preferred embodiment includes a pair of laterally disposed faces 34,34A connected by a plurality of lateral braces 62. A vertical angle 60 below the horizontal is defined by the top edge 59 of the faces 34,34A. The angle 60 is substantially equal to the range of motion of the pivoting support means 78 of the continuous passive motion cervical spine therapy device 10 below the horizontal, as is discussed below. In the preferred embodiment, the angle 60 is substantially fifteen (15) degrees, but may be varied as required. The connections between the faces 34,34A and the lateral braces 62 as described may be of a method commonly understood such as welding or bolting, but may also include methods not yet known.

The body support means 14 is provided for supporting the body a patient. The body support means 14 includes at least a first stationary support means 64 and at least one pivoting support means 78. The first stationary support means 64 is provided to support at least a portion of the back of the patient and to act as a reference point for the displacement of the pivoting support means 78. The first stationary support means 64 is connected to the frame means 12 along the top edge 59 thereof such that the first stationary support means 64 is elevated above the frame means 12. The first stationary support means 64 of the preferred embodiment has a substantially rectangular configuration and is dimensioned to comfortably support a patient of a selected size. In the preferred embodiment, the first stationary support means 64 is substantially planar and is fabricated from a rigid material such as wood, sheet metal, or the like. A cushion 76 may be provided to attach to the top side 74 for the comfort of the patient, especially when extended use is required.

A second stationary support means 210 and associated frame 212 may be provided for supporting the lower body of a patient. The second stationary support means 210 may be attached to the frame 12. It is also foreseeable that the second stationary support means 210 is an existing table, one end of the table being placed in abutment with the first stationary support means 64 proximate the first side 70.

Figure 5:
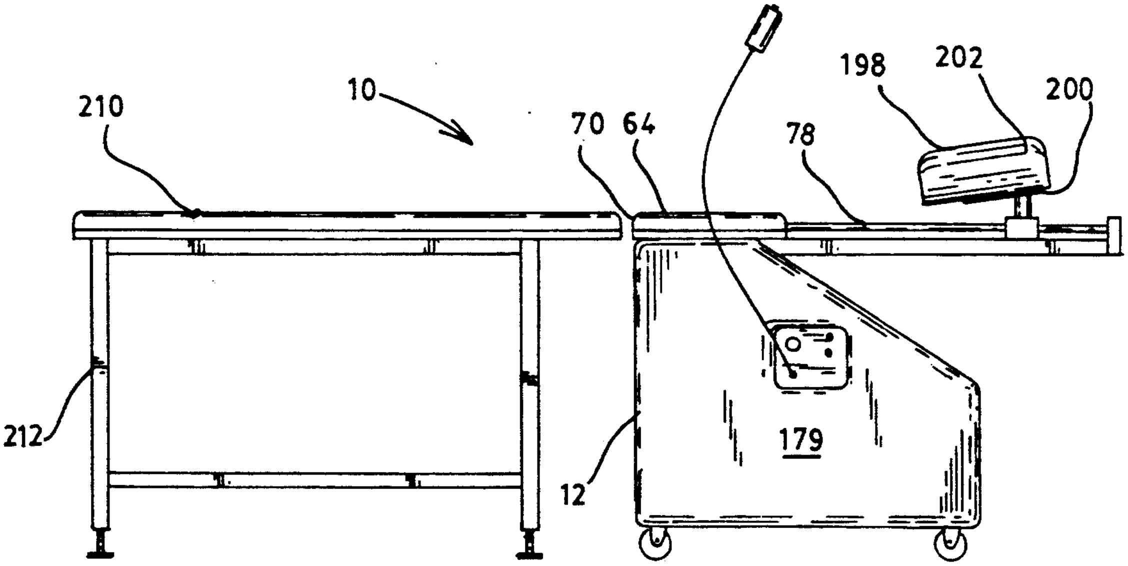
FIG. 5 is a front elevation view of a an alternate embodiment of the continuous passive motion cervical spine therapy device constructed in accordance with several features of the present invention.

A pivoting support means 78 is provided for supporting the head of a patient. As depicted in FIG. 5, a headrest 198 is provided for supporting a patient's head during therapy. The headrest 198 is slidably connected to an arm 204 such that the position of the headrest 198 with respect to the first stationary support means 64 may be adjusted to adapt to various sizes of patients and to prevent movement between the patient's head and the pivoting support means 78 during exercise. As the pivoting support means 78 is moved in either direction away from the horizontal, the headrest 198 is moved away from the first stationary support means 64 due to the friction between the patient's head and the headrest 198.

Figure 6:
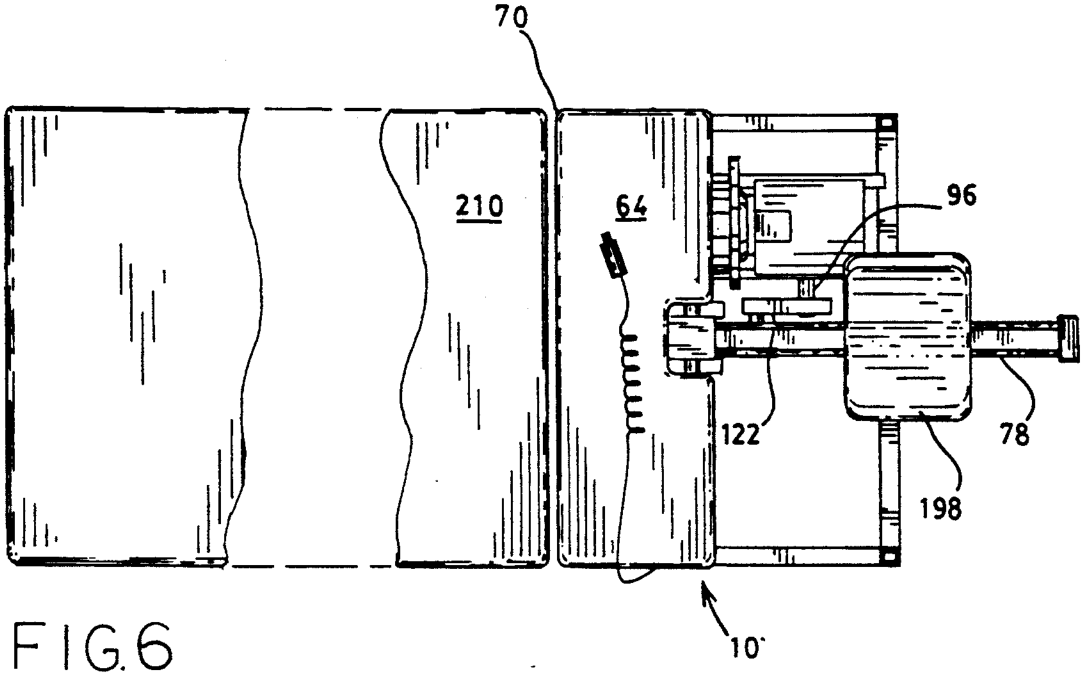
FIG. 6 is a partial top plan view of the present invention as shown in FIG. 5.

As shown in FIGS. 5 and 6, the headrest 198 is an upwardly curved member for receiving the head of a patient. The headrest 198 of the preferred embodiment includes a rigid member 200 fabricated from a material such as wood or sheet metal. A cushion 202 may be provided to cover the pivoting support means 78 for the comfort of the patient.

Figure 8:
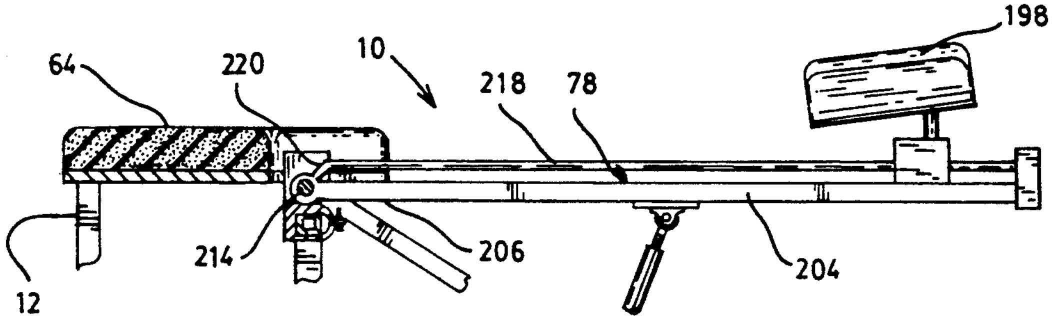
FIG. 8 is a partial front elevation view, shown partially in section, of the pivoting support means as shown in FIG. 5.

The arm 204 is pivotally attached at one end 206 to a support rod 214, which is in turn fixed to the frame 12 such that displacement of the pivoting support means is limited to a pivoting movement about the axis of the support rod 214. Such displacement will substantially limit the movement of the headrest 198 to vertical movement. A more detailed depiction of the configuration of the second pivoting support means 78 is found in FIG. 8, which is to be described below.

Figure 7:
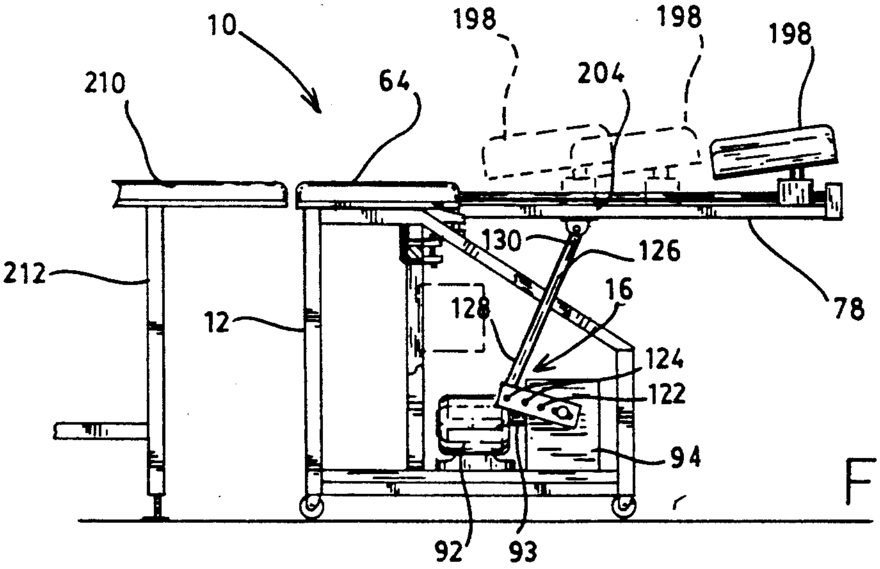
FIG. 7 is a partial front elevation view of the present invention as shown in FIG. 5.

As shown in FIGS. 6 and 7, a drive means 16 is provided for selectively oscillating the pivoting support means 78. The drive means 16 is powered by a selected motor 92 commonly used in the art. In the preferred embodiment, the rotational velocity of the motor 92 may be variably controlled. The first end 98 of a drive shaft 96 is connected to the motor 92, the second end 100 of the drive shaft 96 being connected to a pivoting support displacement means 18. In the preferred embodiment, a transmission 94 is connected between the motor 92 and the drive shaft 96 for controlling the rotational velocity of the drive shaft 96 in relation to the rotational velocity of the motor 92. The drive means 16 of the preferred embodiment is connected to the top 104 of a plate 102 with conventional means such as welding or bolting, the plate 102 being attached to at least one lateral brace 62.

A pivoting support displacement means 18 is provided for oscillating the pivoting support means 78. The drive shaft 96 is connected to a cam 22, thus as the motor 92 is operated, rotating the drive shaft 96, the cam 122 is likewise rotated. The first end 128 of a push rod 126 is journaled to the cam 122 eccentrically such that as the cam 122 is rotated, the first end 128 of the push rod 126 is moved in a circular direction.

In the preferred embodiment, the cam 122 defines a threaded opening 124 dimensioned to receive a selected bolt 132. The first end 128 of the push rod 126 has a substantial "eye" configuration dimensioned to loosely receive the selected bolt 132 inserted into the cam 122. The second end 130 of the push rod 126 is journally connected to the bottom side 86 of the pivoting support means 78 a distance 138 from the first end 80 so that as the first end 128 of the push rod 126 is moved in a circular motion, the second end 130 of the push rod 126 and the pivoting support means 78 are displaced vertically. The second end 130 of the push rod 126 of the preferred embodiment defines a substantial "eye" configuration and is dimensioned to be received by a clevis 134 and held in place with a selected pin 136, bolt or the like.

FIG. 7 illustrates more clearly the operation of the continuous passive motion cervical spine therapy device 10 by isolating the drive means 16 and pivoting support displacement means 78. A number of the components have been omitted from the figure to aid in clarifying such operation. As the motor 92 is operated, a shaft 93 is rotated, the shaft 93 in turn engaging a transmission 94. The transmission 94 selectively reduces or increases the rotational velocity output to the cam 122. As the cam 122 is rotated, the push rod 126 is displaced at one end 128 in a circular direction. A second end 130 of the push rod 126 is pivotally connected to the pivoting arm 204, thereby yielding a substantially vertical displacement above and below the horizontal upon the rotation of the cam 122.

Figure 9:
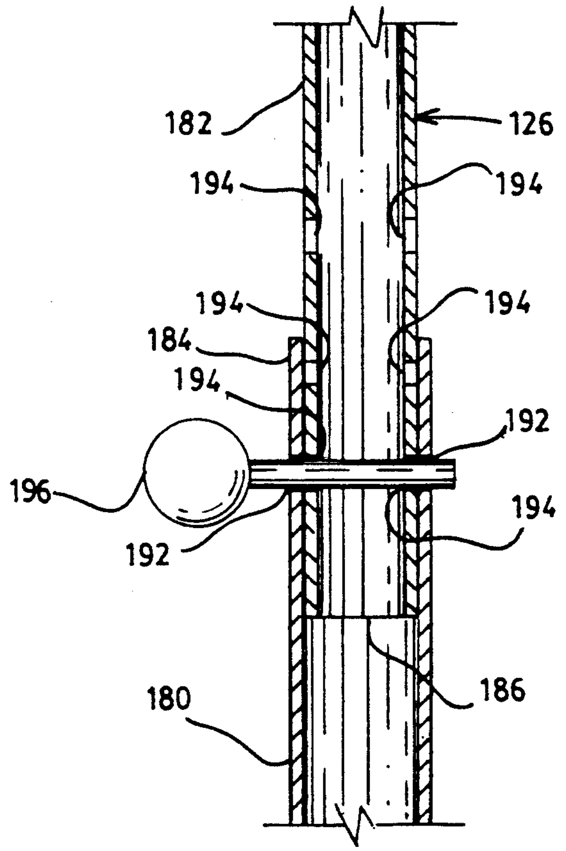
FIG. 9 is a partial front elevation of the push rod of the continuous passive motion cervical spine therapy device of the present invention showing the length adjusting means.

In the embodiment shown in FIG. 9, the push rod 126 includes a first leg 180 and a second leg 182, the first and second legs 180,182 being connected in telescoping fashion about the second and first ends 184,186, respectively. As shown, the first leg second end 184 defines a through hole 192 to cooperate with a through hole 194 defined by the second leg first end 186 in order to receive a pin 196 to selectively secure the first and second legs 180,182 during transport or as otherwise required.

In the preferred embodiment, a plurality of through openings 194 is defined by the second leg first end 186, the openings 194 being spaced linearly apart such that the length of the push rod 126 may be selectively adjusted. The selective adjustability of the length of the push rod 126, it will be seen by one skilled in the art, serves to adjust the relative magnitudes of displacement above and below the horizontal. When the push rod 126 is selectively shortened, the pivoting support means 78 will be displaced a greater distance below the horizontal and a lesser distance above the horizontal, thus producing more flexion than extension. Selectively lengthening the push rod 126 will yield an opposite result. It will be seen that varying the length of the push rod 126 will not substantially effect the overall range of motion of the pivoting support means 78.

A displacement adjustment means 20 is connected to the pivoting support displacement means 18 for selectively altering the amplitude of displacement. In the preferred embodiment, a plurality of openings 140 is defined by the cam 122, the openings being spaced apart radially away from the axle 116. The openings 140 are threaded to receive the selected bolt 132 used to attach the push rod 126 as described above. The opening 142 spaced farthest from the axle 116 has the greatest eccentricity and therefore will yield the greatest displacement of the pivoting support means 78. Likewise, the opening 144 spaced closest to the axle 116 is the least eccentric and will therefore yield the least displacement. It will be seen that varying the connection of the push rod 126 to the different openings 140 will not substantially effect the relative displacements above and below the horizontal, but will be effective in varying the overall range of motion of the pivoting support means 78.

It is envisioned that the displacement adjustment means 20 may alternatively be connected to the pivoting support means 78 proximate the push rod second end 130 if required, the amplitude adjustment being a resultant of varying the distance 138 between the push rod second end 130 and the pivoting support means first end 80. Though not shown, the displacement adjustment means 20 may be carried by the bottom 86 of the pivoting support means 78. In this embodiment, a linear member is affixed to the pivoting support means 78, the linear member defining a plurality of openings spaced apart along the longitudinal axis such as to allow for the selective adjustment of the distance 138. It will be seen that as the distance 138 is increased, the displacement will be smaller.

A control box 22 is provided for the location of the motor controls. The control box 22 includes at least an on/off switch 150 for the selective operation of the motor 92 and a speed regulator 152 for adjusting the speed of the motor 92. In the preferred embodiment, the control box 22 is connected to the frame means 12 proximate the first side panel 34 in a conventional manner such as by bolting or welding. The control box 22 of the preferred embodiment includes a junction box 146 and a cover plate 148. The junction box 146 and cover plate 148 are fabricated from a rigid or semi-rigid material such as metal or plastic. In the preferred embodiment, the junction box 146 is of a type readily available in the market.

A patient control means 24 is provided such that a patient may remotely control the speed of the drive means 16 while using the continuous passive motion cervical spine therapy device 10. The patient control means 24 includes an extension cord 154 with a control button 156 at one end. The control button 156 of the preferred embodiment is configured to be easily held by the user such that the desired exercise may be performed without requiring the patient to alter his position during exercise. The control button 156 is designed to function at least as a remote on/off switch 150 and conceivably as a speed control 152 or other desired function. In the preferred embodiment, the patient control means 24 is connected proximate the control box 22 with a plug-in type jack 158 or other conventional method.

An emergency stopping means 26 is provided to interrupt operation of the continuous passive motion cervical spine therapy device 10 when required. In the preferred embodiment, the emergency stopping means 26 is carried by the control box 22 and includes an on/off switch 160 designed to override all other controls in order to arrest the movement of the pivoting support means 78. The emergency stopping means 26 may be used when the patient feels an excess of discomfort or when a malfunction occurs or the patient is otherwise unable to stop the continuous passive motion cervical spine therapy device 10.

A mobilization means 30 is provided such that the continuous passive motion cervical spine therapy device 10 may be easily transported. In the preferred embodiment, the mobilization means 30 includes a plurality of casters 170 which are commonly known in the art. In this embodiment, the casters 170 are connected to the frame means 12 such as to engage a support surface 32. Casters 170 are attached to the frame means 12 at least proximate the first ends 44 of the frame means first and second vertical members 42. The mobilization means 30 of the preferred embodiment includes braking means to prevent the continuous passive motion cervical spine therapy device 10 from unselected movement along the support surface 32. The casters 170 of the preferred embodiment include wheel locks 172 which may be engaged by pressing one end 174 and disengaged by pressing the opposing end 176.

As illustrated in FIG. 5, the components carried within the frame 12 may be provided with a cover 179 for the protection of both the components carried by the frame 12 and those persons being exercised by, who are operating, or who are near the continuous passive motion cervical spine therapy device 10 during operation of the same.

From the foregoing description, it will be recognized by those skilled in the art that a continuous passive motion cervical spine therapy device offering advantages over the prior art has been provided. Specifically, the continuous passive motion cervical spine therapy device provides a means for passively exercising the muscle groups especially surrounding the cervical spine for postoperative and other rehabilitative therapy such as to allow normal collagen formation to occur, thus minimizing scarring and allowing a faster return to normal function and development of strength in both the muscles of function as well as the secondary support system.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, We claim:

1. A continuous passive motion cervical spine therapy device for passively exercising the muscle groups surrounding the spine for postoperative and other rehabilitative therapy, said continuous passive motion cervical spine therapy device comprising:

a frame for structurally supporting said continuous passive motion cervical spine therapy device and any loads applied thereto;

at least one stationary support member secured to said frame for supporting at least a portion of the back of a user;

a pivoting support member for supporting the head of a user, said pivoting support member being pivotally connected about one end to said frame proximate said stationary support member, said pivoting support member including a head support connected along a pivotally connected arm, said arm being pivotally connected at one end to said frame such as to be pivotal about a substantially horizontal axis both above and below a substantially horizontal plane a selected angle, said head support slidably engaging said pivoting arm such as to yield the placement of said head support a selected distance from said stationary support member and to allow for unencumbered movement of said head support in directions toward and away from said stationary support member during operation of said continuous passive motion spine therapy device; and a drive means for selectively oscillating said pivoting support member about said pivotally connected end a selected angle with respect to said substantially horizontal plane, said drive means including a selected motor with a drive shaft connected to at least one pivoting support displacement member, said pivoting support displacement member including at least a push rod being journally connected at one end to said displacement adjusting member at a selected location along a length thereof, said displacement adjusting member being secured to said drive means such as to yield a substantially vertical displacement of said push rod at a distal end, said distal end of said push rod being journally connected to said pivoting support member, said one end of said push rod being selectively moveable along said length of said displacement adjusting member in order to adjust the amplitude of said substantially vertical displacement.

2. The continuous passive motion cervical spine therapy device of claim 1 wherein said displacement adjusting member includes an attachment rod defining a plurality of linearly spaced apart openings for attaching said one end of said push rod.

3. The continuous passive motion cervical spine therapy device of claim 1 wherein said push rod includes a length adjusting member for selectively adjusting a relative displacement between an angle above said substantially horizontal plane and an angle below said substantially horizontal plane.

4. The continuous passive motion cervical spine therapy device of claim 1, said continuous passive motion cervical spine therapy device including a first stationary support member secured to said frame for supporting at least a portion of the back of a user, and a second stationary support member for supporting at least the upper legs of a user.

5. A continuous passive motion cervical spine therapy device for passively exercising the muscle groups surrounding the spine for postoperative and other rehabilitative therapy, said continuous passive motion cervical spine therapy device comprising:

a frame for structurally supporting said continuous passive motion cervical spine therapy device and any loads applied thereto;

at least one stationary support member secured to said frame for supporting at least a portion of the back of a user;

a pivoting support member for supporting the head of a user, said pivoting support member being pivotally connected about one end to said frame proximate said stationary support member, said pivoting support member including a head support connected along a pivotally connected arm, said arm being pivotally connected at one end to said frame such as to be pivotal about a substantially horizontal axis both above and below a substantially horizontal plane a selected angle, said head support slidably engaging said pivoting arm such as to yield the placement of said head support a selected distance from said stationary support member and to allow for unencumbered movement of said head support in directions toward and away from said stationary support member during operation of said continuous passive motion spine therapy device; and a drive means for selectively oscillating said pivoting support member about said pivotally connected end a selected angle with respect to said substantially horizontal plane, said drive means including a selected motor with a drive shaft connected to at least one pivoting support displacement member, said pivoting support displacement member including at least a push rod and a displacement adjusting member, said displacement adjusting member at a selected location along a length thereof, said displacement adjusting member being secured to said drive means such as to yield a substantially vertical displacement of said push rod at a distal end, said distal end of said push rod being journally connected to said pivoting support member, said one end of said push rod being selectively moveable along said length of said displacement adjusting member in order to adjust the amplitude of said substantially vertical displacement, said displacement adjusting member including an attachment rod defining a plurality of linearly spaced apart openings for attaching said one end of said push rod, said push rod including a length adjusting member for selectively adjusting a relative displacement between an angle above said substantially horizontal plane and an angle below said substantially horizontal plane.

6. The continuous passive motion cervical spine therapy device of claim 5 which further comprises a patient control member for allowing a patient to remotely and selectively vary the speed of said drive means.

7. The continuous passive motion cervical spine therapy device of claim 5 which further comprises an emergency stopping member for stopping said drive means as required.

8. The continuous passive motion cervical spine therapy device of claim 5, said continuous passive motion cervical spine therapy device including a first stationary support member secured to said frame for supporting at least a portion of the back of a user, and a second stationary support member for supporting at least the upper legs of a user.

9. A continuous passive motion cervical spine therapy device for passively exercising the muscle groups surrounding the spine for postoperative and other rehabilitative therapy, said continuous passive motion cervical spine therapy device comprising:

a frame for structurally supporting said continuous passive motion cervical spine therapy device and any loads applied thereto;

at least one stationary support member secured to said frame for supporting at least a portion of the back of a user;

a pivoting support member for supporting the head of a user, said pivoting support member being pivotally connected about one end to said frame proximate said stationary support member, said pivoting support member including a head support connected along a pivotally connected arm, said arm being pivotally connected at one end to said frame such as to be pivotal about a substantially horizontal axis both above and below a substantially horizontal plane a selected angle, said head support slidably engaging said pivoting arm such as to yield the placement of said head support a selected distance from said stationary support member and to allow for unencumbered movement of said head support in directions toward and away from said stationary support member during operation of said continuous passive motion spine therapy device;

a drive means for selectively oscillating said pivoting support member about said pivotally connected end a selected angle with respect to said substantially horizontal plane, said drive means including a selected motor with a drive shaft connected to at least one pivoting support displacement member, said pivoting support displacement member including at least a push rod and a displacement adjusting member, said push rod being journally connected at one end to said displacement adjusting member at a selected location along a length thereof, said displacement adjusting member being secured to said drive means such as to yield a substantially vertical displacement to said push rod at a distal end, said distal end of said push rod being journally connected to said pivoting support member, said one end of said push rod being selectively moveable along said length of said displacement adjusting member in order to adjust the amplitude of said substantially vertical displacement, said displacement adjusting member including an attachment rod defining a plurality of linearly spaced apart openings for attaching said one end of said push rod, said push rod including a length adjusting member for selectively adjusting a relative displacement between an angle above said substantially horizontal plane and an angle below said substantially horizontal plane;

a patient control member for allowing a patient to remotely and selectively vary the speed of said drive means; and an emergency stopping member for stopping said drive means as required.

10. The continuous passive motion cervical spine therapy device of claim 9 which further comprises a mobilization member for enabling said continuous passive motion cervical spine therapy device to be easily transported as desired.

11. The continuous passive motion cervical spine therapy device of claim 9, said continuous passive motion cervical spine therapy device including a first stationary support member secured to said frame for supporting at least a portion of the back of a user, and a second stationary support member for supporting at least the upper legs of a user.

* * * * *